(12) United States Patent
Pan et al.

(10) Patent No.: US 7,978,324 B2
(45) Date of Patent: Jul. 12, 2011

(54) MULTI-CHANNEL ARRAY SPECTROMETER AND METHOD FOR USING THE SAME

(75) Inventors: Jian-gen Pan, Hangzhou (CN); Qian Li, Hangzhou (CN)

(73) Assignee: Everfine Photo-E-Info Co., Ltd., Hangzhou (CN)

( * ) Notice: Subject to any disclaimer, the term of this patent is extended or adjusted under 35 U.S.C. 154(b) by 664 days.

(21) Appl. No.: 12/005,945

(22) Filed: Dec. 27, 2007

(65) Prior Publication Data

US 2008/0259318 A1  Oct. 23, 2008

(30) Foreign Application Priority Data

Apr. 17, 2007  (CN) .......................... 2007 1 0068109
Jun. 15, 2007  (CN) .......................... 2007 1 0069325

(51) Int. Cl.
*G01J 3/28*  (2006.01)
(52) U.S. Cl. ....................................... 356/328
(58) Field of Classification Search .............. 356/72–73, 356/328
See application file for complete search history.

(56) References Cited

U.S. PATENT DOCUMENTS

| 4,060,327 | A | * | 11/1977 | Jacobowitz et al. | .......... 356/328 |
| 4,205,229 | A | * | 5/1980 | Frosch et al. | ................. 356/328 |
| 5,112,125 | A | * | 5/1992 | Neumann | ..................... 356/328 |
| 5,159,199 | A | * | 10/1992 | LaBaw | ........................... 356/328 |
| 2003/0232445 | A1 | * | 12/2003 | Fulghum, Jr. | ................. 436/172 |

FOREIGN PATENT DOCUMENTS

CN   1896722   1/2007

OTHER PUBLICATIONS

The first Office Action issued in corresponding Chinese Application No. 200710069325.5, issued Jun. 28, 2010—4 pages.

* cited by examiner

*Primary Examiner* — Kara E Geisel
(74) *Attorney, Agent, or Firm* — Hamre, Schumann, Mueller & Larson, P.C.

(57) ABSTRACT

A multi-channel array spectrometer combines a spectral measurement system and a reference detector which measures photometric or radiometric qualities. High accuracy photometric or radiometric measurement of a wide dynamic range can be achieved by correcting measurement results of the reference detector with a spectral correction factor. The multi-channel array spectrometer comprises a bandpass filter wheel holding a set of bandpass filters and an open hole. The wheel is placed between an entrance slit and gratings. A test light beam passes through a turret of the bandpass filters. The test light beam can be precisely measured band by band. The spectrometer can also quickly and accurately measure a plurality of test light sources having similar spectral characteristics by using the stray light correction factor.

8 Claims, 4 Drawing Sheets

MULTI-CHANNEL ARRAY SPECTROMETER AND METHOD FOR USING THE SAME

FIELD

This disclosure refers to a multi-channel array spectrometer whose detector is an array detector such as a charge-coupled device (CCD) or a photodiode array (PDA) and a method for using the multi-channel array spectrometer for spectra, calorimetric, photometric and radiometric measurement of light and radiation.

BACKGROUND

Spectrometers are used for the spectral intensity distribution measurement of light and radiation. They are widely used in the fields of light source measurement, color measurement, chemical analysis and so on. Existing multi-channel array spectrometers have advantages of having much higher measurement speed over conventional scanning spectrometers. It takes only several milliseconds to complete a measurement. However, the existing multi-channel array spectrometers still have some disadvantages that cannot be easily resolved. Among these disadvantages, dynamic range limitation and stray light performance are the two major issues which bring challenges to designers and manufacturers.

A photoelectric device of a multi-channel array spectrometer is an array detector such as CCD or PDA. Pixels of the array detector detect the entire spectrum simultaneously, and convert them to electrical signals. The signal of each pixel is proportional to the intensity of light incident on it. After calibration against a standard source with known spectral power distribution, the spectrometer can measure the spectral power distributions of a test light source.

Integration of the spectral power distribution is radiometric quantity of the test light source in an integrated wavelength range. The integration of the spectral power distribution weighted with $V(\lambda)$ function is photometric quantity of the test light source, where $V(\lambda)$ function is the International Commission on Illumination (CIE) standard spectral luminous efficiency function. Thus, the radiometric quantity or photometric quantity of the test light source can be measured.

The photoelectric device of the multi-channel array spectrometer, CCD or PDA, has a narrow dynamic range. As a result, the responsivity curves of the photoelectric device have non-linear problems. The signals of the practical pixels are not strictly proportional to the intensity of the light incident on them. The non-linear problem also occurs along with the integration time. Thus, errors occur in measurement using existing multi-channel array spectrometer.

The radiometric or photometric quantity can also be measured by a broad-band radiometer or photometer detector: a signal from the detector of photoelectric device is proportional to the radiometric or photometric quantity of the test light source. The photoelectric device is always a silicon photodiode. The silicon photodiode can have good linearity in a wide dynamic range. Good silicon photodiodes can reach <0.2% in 8 orders of magnitude. However, the accuracy of radiometric or photometric measurement depends on the relative spectral responsivity of the detector. For a photometer detector, its relative spectral responsivity should precisely match $V(\lambda)$. For a radiometer detector, its relative spectral responsivity should precisely match a flat straight line, that is, its spectral responsivity has the same sensitivity at every wavelength. To meet these requirements, proper optical filters are mounted before the silicon photodiode in the detector. This technique is complicated and the cost is high.

Besides the linear dynamic range, stray light level is another important parameter for multi-channel array spectrometers. Stray light is the radiation at wavelengths other than the one being measured, which enters the detector at the same time and attribute to measurement errors. This parameter is important for most applications, particularly in the following situations.

Line spectrum emissions have large empty regions in spectral distribution.

Spectrometer calibration is usually performed with standard illuminant A which exhibits 25 times more energy at 780 nm than at 380 nm. So during calibration, an instrument response at 380 nm will be over-estimated due to stray light.

Stray light can be caused by grating blemishes, dust on grating and mirror surfaces, high order light and re-entrant light caused by multi-reflection in the optical bench and so on. Good detail design can reduce stray light to a reasonable level, for example, by using a full-sealed structure, painting the inner of the instrument matt black and setting diaphragms in front of the collimating mirror and gratings, and so on. However, further improvements are needed for best accuracy. The simplest improvement is to introduce a turret of bandpass filter to attenuate spectral components well away from the tuned wavelength, and double monochromators are the best way to reject stray light. The filter turret and the double monochromators are mostly applied to scanning type instruments currently. However, they cannot be easily used for increasing accuracy of multi-channel array spectrometers. Thus, one of the limitations to the high speed array type arises from stray light response.

Filters including longpass filters, shortpass filters or bandpass filters are usually introduced into the high speed array spectrometer. The longpass filters are the most applied ones which are installed between a light entrance aperture and an entrance slit, behind the entrance slit, or on front of the array detector. The longpass filters are usually used to reject higher order responses. However, they have many shortages because by only using the longpass filters, the stray light caused by the multi-reflection in the optical housing can not be rejected. Also, there will be errors in calibration and measurement of above mentioned illuminant A like light which has lower intensity in short wavelength ranges. The shortpass filters, bandpass filters and linear variable filters (LVF) that are longpass, short-pass and variable-bandwidth filters, are sometimes introduced in the multi-channel array spectrometers for spectrally shaping the excitation energy from broadband sources. They are usually installed on the front of the array detector. While these filters also have limitations, for example, because they are installed at the end part of the test optical path, the most important limitation is that they can not prevent producing of stray light as the broadband light transmitting in the optical housing.

SUMMARY

To overcome the problems in the existing high speed spectrometers, for example, linear dynamic ranges and stray light rejection, this disclosure provides a multi-channel array spectrometer having a wide dynamic range with high linearity, low stray light and high accuracy, and a method for using the multi-channel array spectrometer, especially regarding low stray light measurement of a plurality of test light beams with similar spectral characteristics.

In one embodiment, a multi-channel array spectrometer comprises a housing, a light collection means mechanically connected to the housing to collect and transfer a test light beam from a test light source to the housing. Optical elements inside the housing comprise: an entrance slit, at least one grating and at least one array detector. The optical path extending from the light collection means to the housing and passing through the entrance slit to the grating and at last received by the array detector. These elements are used to measure spectral power distribution of the test light source. A reference detector for measuring radiometric or photometric quantities of the test light sources is located in the housing. The housing further includes a microcomputer being electrically connected to the array detector and the reference detector. Analogue electrical signals of the array detector and the reference detector are converted into digital signals by an analog-to-digital converter (A/D converter) and then transmitted to the microprocessor. A photoelectric device of the reference detector can be a silicon photodiode. The array detector can be a CCD or a PDA. Information of the spectral power distribution measured by the array detector and the photometric or radiometric parameter measured by the reference detector can be processed by special software so as to get a spectral correction factor to correct the photometric or radiometric parameter.

In the above described embodiment, a reference detector can have a wide linear dynamic range. And measured results of the reference detector can be corrected with high accuracy by combining the spectral power distribution data of test light source.

The multi-channel array spectrometer of this disclosure has many advantages. For example, it has a wide dynamic range, good linearity, accurate photometric or radiometric measurement even when a relative spectral responsivity of the reference detector is not precisely matched to $V(\lambda)$ or a flat straight line.

In another embodiment, the multi-channel array spectrometer can have good stray light rejection performance. The multi-channel array spectrometer comprises a housing, a light collection means introducing a test light beam from a test light source into the housing. Optical elements inside the housing comprise a entrance slit, at least one grating for optical dispersion, an optical focusing system, at least one array detector, and a bandpass filter wheel holding a set of bandpass filters and an open hole. An optical path is extended from the light collection means to the array detector in the housing. The bandpass filter wheel is configured such that the wheel can be rotated and one of the bandpass filters or the open hole can be easily switched into a test optical path between the entrance slit and the gratings. A microprocessor and electrical circuits are located inside the housing. They are used to control working status of the optical elements and the rotation of the bandpass filter wheel and to record and process the measured data.

There are at least three measurement modes for using the multi-channel array spectrometer: 1) quick measurement for one test light source: measure the entire spectrum of a light beam of a test light source simultaneously without any bandpass filters in the bandpass filter wheel; 2) precise measurement for one test light source: rotate the bandpass filter wheel to let the test light beam of the test light source pass through the bandpass filters in turn, measure the test light band by band; and 3) precise and quick measurement for a plurality of test light sources with similar spectral characteristics: measure a typical test light source in the above described two measurement modes respectively and calculate a stray light correction factor by using the measured results of the typical test light source in the two modes, quickly measure the similar test light sources in the quick measurement mode at the same condition as for measuring the typical test light source, and correct the measured results by using the calculated stray light correction factor.

In this embodiment, a broadband light is firstly tuned to be a relative narrow band light by a turret of the bandpass filters. This can effectively reject the stray light caused by multi-reflection of a far-filed light such as a scanning monochromator spectrometer usually does. The precise measurement mode for one test light beam takes a relative longer time. However, the speed is still much quicker than monochromators which may have the same accuracy. The mode of precise measurement of one test light source can be used in labs.

Because of limit to speed, the precise measurement mode for every test light source may not be productive. Since for test light sources having similar spectral characteristics, the stray light disturbance is similar in one spectrometer, these test light sources can be quickly and accurately measured by using a stray light correction factor calculated from measurement of the typical test light source.

Other techniques are available in this disclosure. In one embodiment, the bandpass filter wheel also can hold at least one density filter which is used to weaken the light intensity and enlarge the measurement dynamic range. In addition, a black filter can also be held in the bandpass filter wheel, the multi-channel array spectrometer does not work when the black filter is placed into the optical path.

In another embodiment, the microprocessor can be connected to an onboard computer. The connection between the microprocessor and the onboard computer is through a communication interface, and the interface can be a Universal Serial Bus (USB), Infrared (IR) or Bluetooth interface. Data and signals can be transmitted between them. The computer controls working status of the microprocessor and processes measurement data.

In another embodiment, the array detector can be a CCD or PDA. The arrays can be linear or two-dimensional ones and the binning mode can be operated for the two-dimensional array, i.e. all pixels in a column are summed electronically. This helps reduce noise significantly and enhances measurement precision. The number of the bandpass filters held in the bandpass field wheel can be varied from 2 to 20 according to the application and mechanical size of the spectrometer. The entire required wavelength range must be covered by the tuned band of the bandpass filters. The tuned bands of the bandpass filters should be overlapped.

In still another embodiment, a density filter wheel holding a set of density filters and an open hole can be further placed in the housing between the entrance slit and the grating. The density filter wheel can be rotated and a certain density filter or the open hole can be easily switched into an optical path. With the density filters, the intensity of optical signals can be reduced. This can largely enlarge the dynamic range of the spectrometer.

In further another embodiment, longpass filters can be placed in the housing in an optical path and close to the entrance slit, or on front of the array detector. The longpass filters are mainly used to reject a higher order effect or balance color. Other filters like shortpass filters, bandpass filters or linear variable filters (LVF) that comprise longpass, shortpass or, variable-bandwidth filters can be applied in front of the array detector to reduce stray light and higher order responses.

In further another embodiment, the light collection means can be a beam collector or a fiber. In case of using a fiber, an end of the light collection means can be a fiber connector connecting the housing and the end for collecting light. The light collection means can also include a cosine corrector and a protecting cover.

In further another embodiment, the bandpass filter wheel and the density filter wheel (if included in the spectrometer) can be driven by a step motor with or without reducer, a servo motor or a DC motor.

In further another embodiment, the grating for dispersion is a plane grating or flat-field concave grating according to its shape and function. The flat-field concave grating can act as both a dispersion element and a focusing element. The grating can also be classified as ruled grating or holographic grating depending on manufacturing process. Generally, the holographic grating introduces less stray light.

In further another embodiment, other optical elements can be included in the housing, for example, a collimating mirror which collimates a emanative light beam to a parallel light beam, a mirror which changes an optical path before the entrance slit, or between the entrance slit and the collimation mirror (if included in the spectrometer) or the grating. A plating film means on the front of part of the array detector can be used to enhance ultraviolet sensitivity of the spectrometer, etc.

A test wavelength range can be visible wavelength from 380 nm~780 nm, or a broadband radiation section in the ultraviolet-visible-near infrared (UV-VIS-nIR) wavelength range, or some other wavelength ranges.

DRAWINGS

The above noted and other features of the disclosure will be better understood from the following detailed description when considered with reference to the accompanying drawings in which.

For simplification purposes, the means appended to the disclosure, and in particular the conventional electronic and computer circuits known in the field (signal acquisition, signal processing, automation, calculation, display, result printing, etc.) have not been represented in the figures.

DETAILED DESCRIPTION

Figure 1:
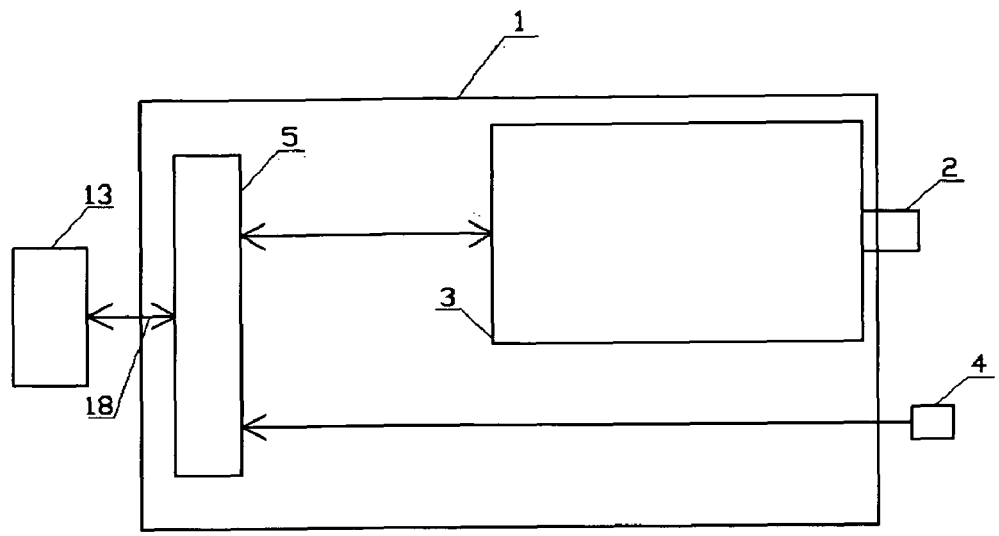
FIG. 1 is a schematic view of an embodiment of a multi-channel array spectrometer.

This disclosure refers to a multi-channel array spectrometer. FIG. 1 shows a block diagram of an embodiment of the disclosure. According to FIG. 1, the multi-channel array spectrometer is generally packed in housing 1. A light collection means 2 is mechanically connected to the housing 1 and gathering a test light beam from a test light source into the housing 1. The test light beam is dispersed and detected in the housing 1 by a so called spectral analyzing system 3 which comprises a grating, an array detector and other optical elements. A reference detector 4 measures photometric or radiometric quantity of the test light source. A photoelectric device of reference detector 4 is a silicon photodiode. A microprocessor 5 is electrically connected to the spectral analyzing system 3 and the reference detector 4. The microprocessor 5 controls the working state of the spectral analyzing system 3 and the reference detector 4. Analogue electrical signals of both the array detector in the spectral analyzing system 3 and the reference detector 4 are converted to digital signals by an A/D converter first, and then transmitted to the microprocessor 5. In the embodiment as shown in FIG. 1, the microprocessor 5 is electrically connected to an onboard computer 13 via a USB communication interface 18.

Figure 2:
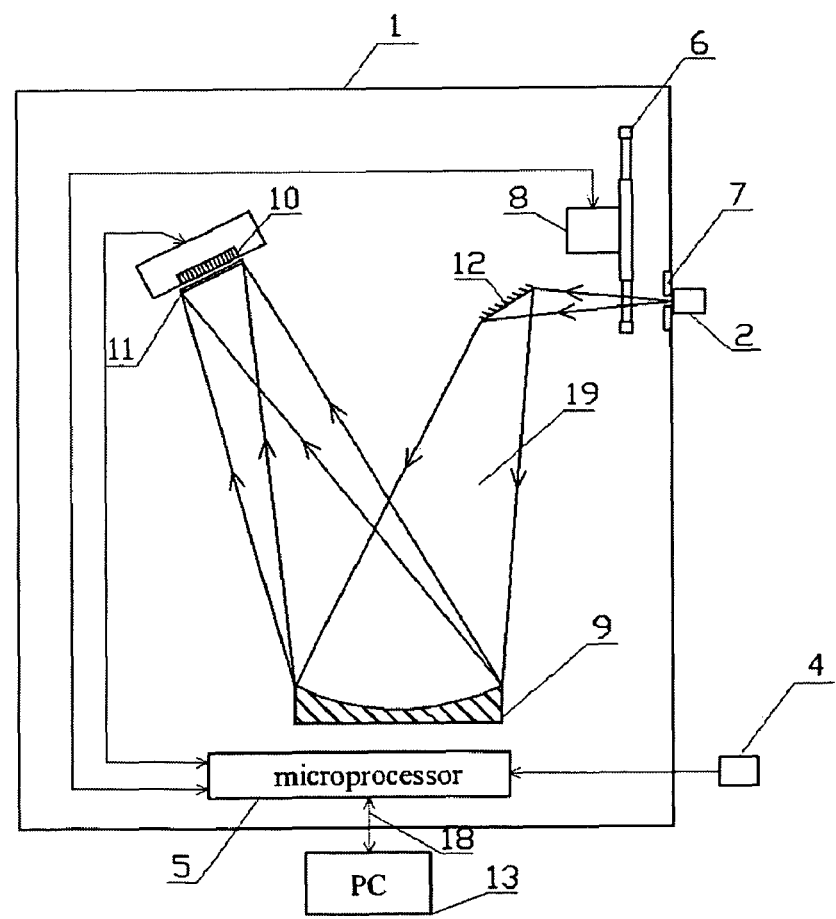
FIG. 2 is a schematic view of an embodiment of a multi-channel array spectrometer.
Figure 3:
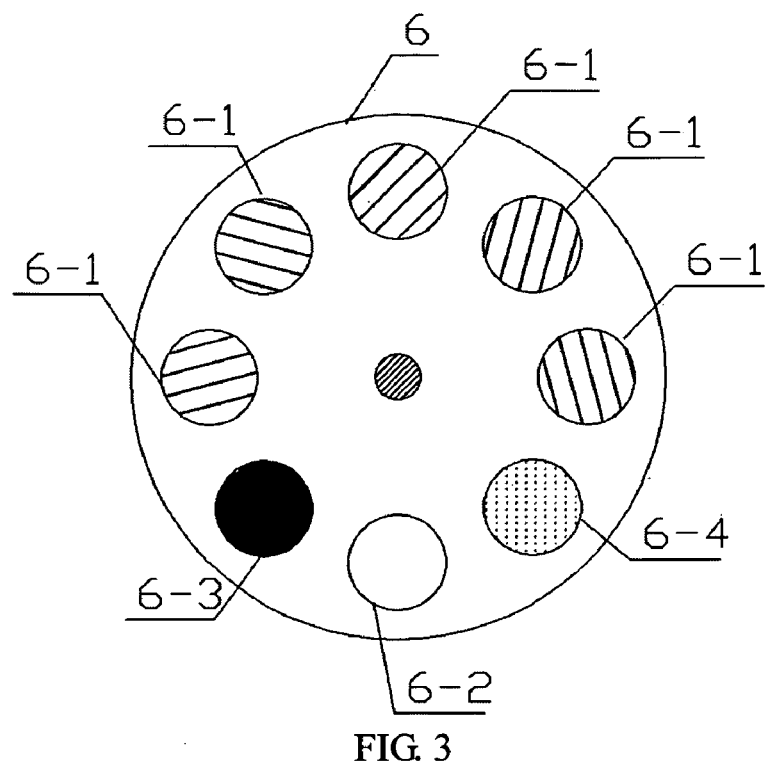
FIG. 3 is a schematic view of a bandpass filter wheel.

FIG. 2 is a detailed sketch of one embodiment of this disclosure. According to FIG. 2, optical signals of a test light source are introduced into the housing 1 via the light collection means 3. An optical path 19 is extended from the light collection means to the array detector in the housing. The test light beam from a test light source follows the optical path 19 which first passes through an entrance slit 7 that is located in the housing 1. The aperture of the entrance slit 7 can be fixed or adjustable. A mirror 12 which changes the direction of the test light beam is placed behind the entrance slit 7. A bandpass filter wheel 6 is placed in the housing 1, behind the entrance slit 7 as shown in FIG. 2. The bandpass filter 6 holds a set of five bandpass filters 6-1, an open hole 6-2, a blind filter 6-3 and a density filter 6-4, as shown in FIG. 3. The bandpass filter 6 can be driven by a motor 8, which can include a reducer. Each of the filters 6-1, 6-3, 6-4 or the open hole 6-2 in the bandpass filter wheel 6 can be switched into the optical path 19. A flat-field concave holographic grating 9 is placed in the optical path 19 as shown in FIG. 2. The flat-field concave holographic grating 9 has two main functions: light dispersion and focusing the dispersed light into an array detector 10. The array detector 10 is a CCD or PDA, which can be a linear or a two dimension array detector. Linear variable filters (LVF) 11 comprising longpass filters, shortpass filters, and bandpass filters can be placed on front of an acceptance area of the array detector 10. The LVF 11 is used to eliminate second- and third-order effects, to limit stray light and to balance spectral intensity in some region. In this embodiment, the microprocessor 5 is placed inside the housing 1 and is electrically connected to the array detector 10, the motor 8 and the reference detector 4. The microprocessor 5 controls the working status of the array detector 10, the motor 8 and the reference detector 4, and receives the measurement data via A/D converters 20 and other circuits of the array detector 10 and the reference detector 4. The microprocessor 5 can also communicate with an onboard computer 13 via a USB interface 18. The microprocessor 5 receives orders from and transfers data to the onboard computer 13.

Figure 4:
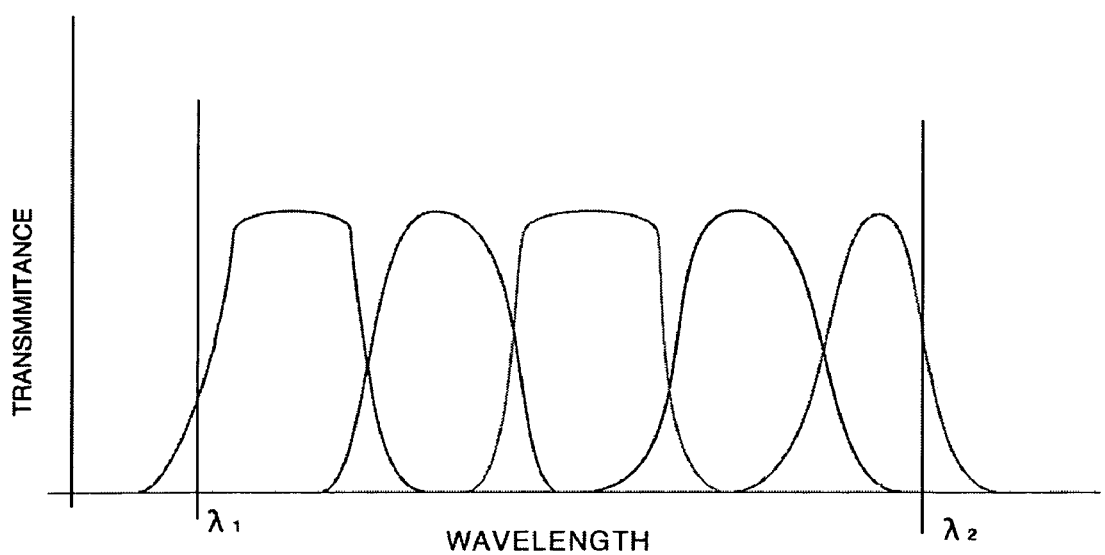
FIG. 4 is a graph of a tuned band of a turret of a bandpass filter.

FIG. 4 is a graph of a spectral tuned band of the bandpass filters 6-1 in the bandpass filter wheel 6. In one embodiment, each of the bandpass filters has a narrow tuned band. The band of each filter overlaps with those of adjacent filters. The wavelength range from $\lambda_1$~$\lambda_2$ to be measured is all covered by the tuned band of these filters 6-1. After passing through one bandpass filter, the test light beam becomes a light beam having narrower band and is then dispersed and detected. The light intensity of the test light beam is reduced by the test light beam pasting through the density filter 6-4, as shown in FIG. 3. It will be appreciated that although the density filter 6-4 reduces the intensity of the test light beam at all wavelength, the density filter 6-4 has spectral transmittance selectivity and it is necessary to calibrate the multi-channel array spectrometer when using the density filter 6-4. The black filter 6-3 blocks the test light beam that enters the housing 1 at all wavelength. The array detector 10 does work when the block filter 6-3 is switched into the optical path 19.

Figure 5:
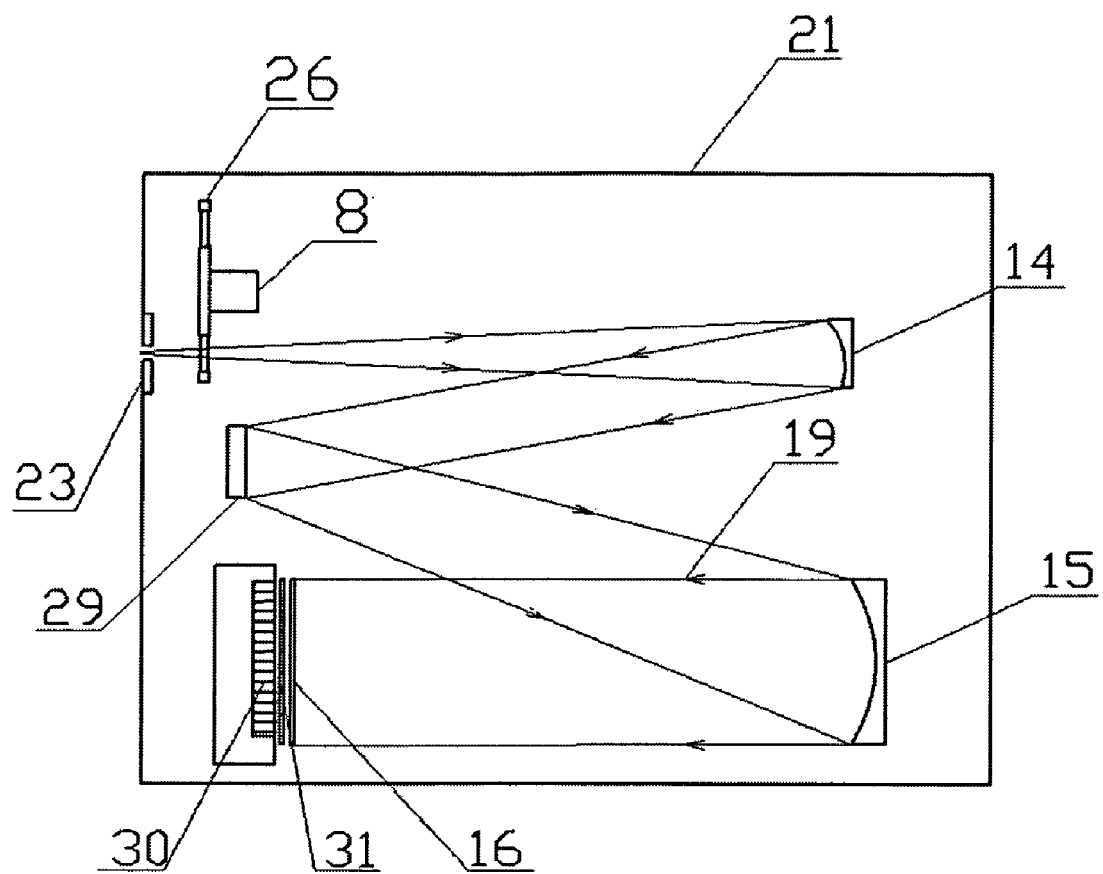
FIG. 5 is a schematic view of another embodiment of a multi-channel array spectrometer.

FIG. 5 illustrates another embodiment of the multi-channel array spectrometer, including a housing 21, where the basic principle and measurement method are the same as that in FIG. 2. A test light beam from a test light source enters the housing 21 and passes through an entrance slit 23. A bandpass filter wheel 26 is placed behind the entrance slit 23, and a filter or an open hole can be easily switched into an optical path 19. A collimating mirror 14 which can focus scatted light to parallel light is placed behind the bandpass filter wheel 26. The collimating mirror 14 also changes the direction of the path of the test light beam. A grating 29 is also placed in the optical path 19. Instead of the flat-field concave grating 9 as shown in the embodiment in FIG. 2, the grating 29 is a plane ruled grating and reflects the dispersed light from the collimating mirror 14 to a focusing mirror 15 which then focuses the spectra on a plane of an array detector 30. The array detector 30 can be a linear array detector. A cylindrical lens 16 is placed before the array detector 30 to focus the light onto detector elements and to increase light-collection efficiency. An LVF 31 can also be placed between the cylindrical lens 16 and the array detector 30.

Figure 6:
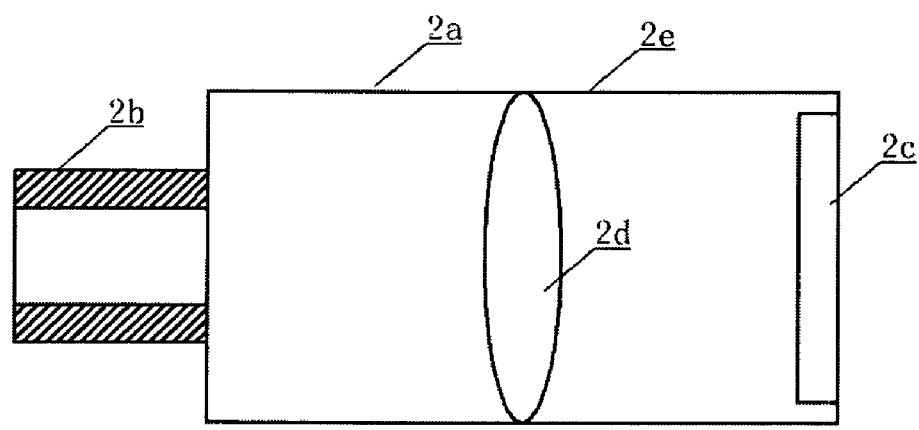
FIG. 6 is a schematic view of a light collection means.

Referring to FIG. 6, an embodiment of the light collection means 2 includes a beam collector 2a. One end of the beam collector 2a is connected to the housing 1 through a connector 2b. A cosine corrector 2c that is fixed in the installation tube 2e is located on the other end of the beam collector 2a. Inside the installation tube 2e, a convex lens 2d is located in the middle as shown in FIG. 6. The convex lens 2d is used to collect the test light beam that has passed through the cosine corrector 2c. The light collection means 2 can also be an optical fiber which can be achieved by utilizing existing technologies. For simplification purposes, this will not be discussed herein.

Generally, there are three methods for measuring spectral power distribution of the test light source: 1) precise measurement of one test light source, band by band, 2) high speed measurement of one test light source, and 3) precise and high speed measurement of a plurality of test light sources with similar spectral characteristics.

At first, the spectrometer needs to be calibrated. According to the measurement methods, the calibration is required in two kinds of situations. In the first kind of situations, a standard illuminant A is used to calibrate the spectrometer band by band with help of the bandpass filters. The calibration coefficient of the ith bandpass filter is $C^i(\lambda)=P(\lambda)_s/M^i(\lambda)_s$, wherein $P(\lambda)_s$ is the known spectral power distribution of the standard illuminant A, $M^i(\lambda)_s$ is the responsivity of the ith bandpass filter of the spectrometer as to the standard illuminant A. In the other calibration situation, the same illuminant A is used when the open hole or the density filter is switched into the optical path 19. The calibration coefficient is $C^0(\lambda) = P(\lambda)_s/M^0(\lambda)_s$, wherein $M^0(\lambda)_s$ is the responsivity of the open hole or the density filter of the spectrometer as to the standard illuminant A.

The precise measurement of one test light source, band by band, is to precisely measure a light beam of one test light source, band by band, by rotating the bandpass filter wheel 6, 26. A light beam of one test light source passes one by one through a turret of each of the bandpass filters. The corresponding tuned wavelength ranges are dispersed and detected. The spectral intensity of the test light beam after being filtered by the ith bandpass filter is $P^i(\lambda)=C^i(\lambda)\cdot M^i(\lambda)$, wherein $C^i(\lambda)$ is the calibration coefficient of the standard illuminant A that has passed through the ith bandpass filter, and $M^i(\lambda)$ is the responsivity of the instrument to the test light source. A low stray light spectral intensity distribution in the entire wavelength range $P(\lambda)$ is obtained by adding the values in every tuned band together.

The high speed measurement of one test light source is the same as that used for the conventional high speed array spectrometers. The opening hole or density filter is switched into an optical path 19, so that the entire wavelength range of the test light source can be measured simultaneously. The spectral intensity distribution can be obtained by $P^0(\lambda)=C^0(\lambda)\cdot M^0(\lambda)$, wherein $C^0(\lambda)$ is the calibration coefficient of the standard illuminant A that has passed through the open hole or the density filter, and $M^0(\lambda)$ is the responsivity of the instrument to the test light source.

The precise and high speed measurement of a plurality of test light beams with similar spectral characteristics comprising:

(a) precisely measure a typical test light source band by band as described above in the method of precise measurement of one light beam of a test light source, band by band. The low stray light spectral intensity distribution of this test light beam is $P(\lambda)_t$;

(b) quickly measure the entire spectra of the typical test light source simultaneously with the open hole or the density filter on the bandpass filter wheel 6, 26 as described above in the method of high speed measurement of one test light source. The spectral intensity distribution of the typical test light source is $P^0(\lambda)_t$;

(c) calculate a stray light correction factor from the result of (a) and (b), which is $$K(\lambda)_{stray} = \frac{P(\lambda)_t}{P^0(\lambda)_t};$$

(d) measure the similar test light sources by using the same method as described in (b), then correct the result by the stray light correction factor. The relatively precise spectral intensity distribution of the similar test light beams can be obtained as $P(\lambda)_u = P^0(\lambda)_u \cdot K(\lambda)_{stray}$, wherein $P^0(\lambda)_u$ is spectral intensity distribution of the similar test light sources that has passed through the open hole.

Figure 7:
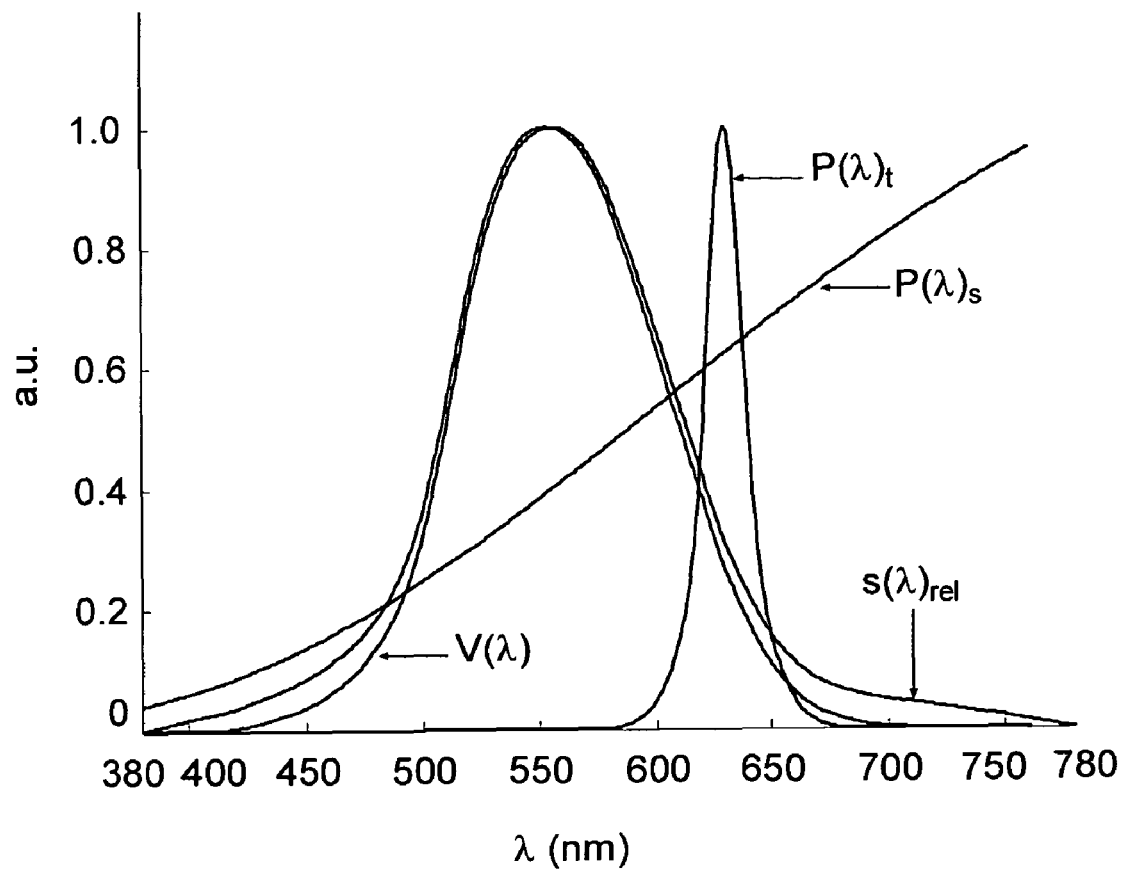
FIG. 7 is a graph of a relative spectral sensitivity curve of a reference detector.

When the array detector is used to measure the relative spectral power distribution of a test light source, the reference detector 4 can be used to measure photometric quantity of the test light source. The test results are transferred to the onboard computer 12. The spectral correction factor can be calculated by the onboard computer 12 according to:

$$k1 = \frac{\int_{380}^{780} P(\lambda)_t V(\lambda)\, d\lambda}{\int_{380}^{780} P(\lambda)_t s(\lambda)_{rel}\, d\lambda} \cdot \frac{\int_{380}^{780} P(\lambda)_s s(\lambda)_{rel}\, d\lambda}{\int_{380}^{780} P(\lambda)_s V(\lambda)\, d\lambda}$$

Where $V(\lambda)$ is the known CIE standard spectral luminous efficacy function, $s(\lambda)_{rel}$ is the known relative spectral responsivity of the reference detector 4, $P(\lambda)_s$ is the known relative spectral power distribution of the standard source against which the reference detector 4 is calibrated, $P(\lambda)_t$ is the measured relative spectral power distribution of the test light source. The known or measured data of $V(\lambda)$, $s(\lambda)_{rel}$, $P(\lambda)_s$ and $P(\lambda)_t$ are all saved in onboard computer 12. In one embodiment, their curves are shown in FIG. 7. The measured photometric results by reference detector 4 are then multiplied with the calculated spectral correction factor k1 to obtain the final measurement results of the photometric quantity of the test light source.

Referring to FIG. 7, $V(\lambda)$ is the CIE standard spectral luminous efficacy function, $s(\lambda)_{rel}$ is the relative spectral responsivity of reference detector 4, $P(\lambda)_s$ is the relative spectral power distribution of the standard source against which the reference detector 4 is calibrated, $P(\lambda)_t$ is the relative spectral power distribution of the test light source. The relative spectral responsivity of the reference detector 4 within the spectral range of 380 nm~780 nm has been measured precisely by other instruments, and is zero out of this range. The relative spectral responsivity of the reference detector 4 is not strictly matched to $V(\lambda)$. The standard source can be a tungsten halogen lamp of 2856 K color temperature. The test light source can be a red LED.

However, when measuring radiometric qualities whose wavelength range is not within a visible range, and the spectral responsivity of the reference detector 6 matches flat curve, the method of correction is more or less the same, except that the equation to calculate the spectral correction factor is $$k2 = \frac{\int_{\lambda 1}^{\lambda 2} P(\lambda)_t \, d\lambda}{\int_{\lambda 1}^{\lambda 2} P(\lambda)_t s(\lambda)_{rel} \, d\lambda} \cdot \frac{\int_{\lambda 1}^{\lambda 2} P(\lambda)_s s(\lambda)_{rel} \, d\lambda}{\int_{\lambda 1}^{\lambda 2} P(\lambda)_s \, d\lambda},$$

where $s(\lambda)_{rel}$ is the known relative spectral responsivity of the reference detector 4, $P(\lambda)_s$ is the known relative spectral power distribution of the standard source against which the reference detector 4 is calibrated, $P(\lambda)_t$ is the relative spectral power distribution of the test light source which is measured by the spectral analyzing system 3 and $\lambda 1 \sim \lambda 2$ is the spectral range of the measured radiometric quantity.

While the multi-channel array spectrometer and the method for using the same has been explained with reference to the specific embodiments of the disclosure, the explanation is illustrative and the invention is limited only by the appended claims.

The invention claimed is:

1. A multi-channel array spectrometer, comprising:
    a housing including an entrance slit, a bandpass filter wheel holding a set of bandpass filters and an open hole, at least one grating and at least one array detector;
    a light collection means mechanically connected to said housing;
    an optical path extending from said light collection means to the array detector in said housing;
    a driving mechanism being mechanically connected to the bandpass filter wheel which drives the bandpass filter wheel so that one of the bandpass filters or the open hole is switched into the optical path; and
    a microprocessor being electrically connected to the array detector and the driving mechanism,
    wherein a number of the bandpass filters held in the bandpass filter wheel is a number within a range from 2 to 20, the bandpass filters including wavelength bands overlapping those of adjacent filters, and a combined wavelength range covering an entire wavelength range of the spectrometer.

2. A multi-channel array spectrometer according to claim 1, further comprising a black filter acting as a shutter that blocks the optical path, the black filter being placed in the bandpass filter wheel.

3. A multi-channel array spectrometer according to claim 1, further comprising at least one density filter being placed in the bandpass filter wheel.

4. A multi-channel array spectrometer according to claim 1, wherein at least one mirror is placed in said housing and in the optical path between the entrance slit and the grating, the mirror being configured for changing the optical path.

5. A multi-channel array spectrometer according to claim 1, further comprising linear variable filters being placed in front of the array detector, the variable filters being at least one selected from the group consisting of longpass filters, shortpass filters, bandpass filters and combination thereof.

6. A multi-channel array spectrometer according to claim 1, wherein the grating is a plane or flat-field concave grating according to a shape of the grating, and the grating is a ruled or holographic grating according to a manufacturing process of the grating.

7. A multi-channel array spectrometer according to claim 1, wherein a measuring wavelength range of the spectrometer is a visible range or a broadband radiation wavelength section in a range of ultraviolet-visible-near infrared wavelengths, which is from 200 nm to 3000 nm.

8. A multi-channel array spectrometer according to claim 1, wherein said microprocessor is electrically connected to a computer such that data can be communicated between said microprocessor and the computer, a communication interface between the microprocessor and the computer including at least one of a Universal Serial Bus connection, an Infrared connection or a Bluetooth interface connection.

* * * * *